(12) United States Patent
Tomohira et al.

(10) Patent No.: US 7,867,514 B2
(45) Date of Patent: Jan. 11, 2011

(54) METHOD FOR STABILIZING PREPARATION

(75) Inventors: Yuso Tomohira, Tokushima (JP); Tadashi Mukai, Naruto (JP); Minoru Kashimoto, Naruto (JP); Masakazu Nagasawa, Tokushima (JP); Tetsuroh Ichiba, Tokushima (JP); Daisuke Kuribayashi, Kakogawa (JP); Yoshikazu Oka, Tokushima (JP); Hajime Toguchi, Nishinomiya (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 770 days.

(21) Appl. No.: 10/276,294

(22) PCT Filed: May 23, 2001

(86) PCT No.: PCT/JP01/04302

§ 371 (c)(1),
(2), (4) Date: Nov. 21, 2002

(87) PCT Pub. No.: WO01/89573

PCT Pub. Date: Nov. 29, 2001

(65) Prior Publication Data

US 2003/0161873 A1    Aug. 28, 2003

(51) Int. Cl.
*A61K 9/14*    (2006.01)
*A61K 9/20*    (2006.01)
*A61K 9/48*    (2006.01)

(52) U.S. Cl. .................. 424/464; 424/451; 424/489
(58) Field of Classification Search .................. 424/484
See application file for complete search history.

(56) References Cited

U.S. PATENT DOCUMENTS

| | | | | |
|---|---|---|---|---|
| 4,666,919 A * | 5/1987 | Ueno et al. | .................. | 514/309 |
| 5,225,204 A * | 7/1993 | Chen et al. | .................. | 424/484 |
| 6,121,271 A * | 9/2000 | Dollings et al. | ............. | 514/269 |
| 6,187,790 B1 * | 2/2001 | Cutler | .................. | 514/312 |
| 6,369,273 B1 * | 4/2002 | Butlin | .................. | 564/202 |
| 6,417,196 B1 * | 7/2002 | Daniel et al. | ................. | 514/310 |
| 7,144,585 B1 * | 12/2006 | Mukai et al. | ................. | 424/452 |
| 2002/0004498 A1 * | 1/2002 | Doherty et al. | ............. | 514/182 |

FOREIGN PATENT DOCUMENTS

| | | |
|---|---|---|
| EP | 0702954 A2 | 3/1996 |
| EP | 0711544 A2 | 5/1996 |
| JP | 07-082126 | 3/1995 |
| JP | 10-130142 | 5/1998 |
| JP | 11-116451 | 4/1999 |
| JP | 11-189531 | 7/1999 |
| JP | 11-189546 | 7/1999 |
| WO | WO97/17951 | 5/1997 |
| WO | WO97/33567 | 9/1997 |
| WO | WO98/00136 | 1/1998 |
| WO | WO99/30714 | 6/1999 |

OTHER PUBLICATIONS

Yamashita et al. "Cilostazol increased heart rate with improvement of activity of daily living in an elderly patient with sick sinus syndrome"; Nippon Ronen lgakkai Zasshi, Aug. 1999; 36(8):561-4.*
Wade et al. "Handbook of Pharmaceutical Excipients" Second Edition, p. 448; 1994.*
Ansel et al. "Pharmaceutical Dosage Forms and Drug Delivery Systems" Seventh Edition, pp. 197-198.*
International Search Report dated Aug. 28, 2002.

* cited by examiner

*Primary Examiner*—Susan T Tran
(74) *Attorney, Agent, or Firm*—Finnegan, Henderson, Farabow, Garrett & Dunner, L.L.P.

(57) ABSTRACT

Disclosed is a method for stabilizing a solid pharmaceutical preparation containing a pharmacological substance and sodium lauryl sulfate, the method comprising incorporating into the preparation at least one member selected from the group consisting of neutral salts, basic salts and basic substances. The preparation containing sodium lauryl sulfate prepared by the method of the invention has superior performance, including high storage stability, suppression of discoloration and deterioration, and prevention of change in its properties, such as the dissolution rate of pharmacological substance from the preparation.

3 Claims, No Drawings

METHOD FOR STABILIZING PREPARATION

FIELD OF THE INVENTION

The present invention relates to a method for stabilizing a solid pharmaceutical preparation containing sodium lauryl sulfate.

BACKGROUND ART

Sodium lauryl sulfate is often incorporated in a solid pharmaceutical preparation because of it possesses useful properties capable of accelerating absorption, facilitating dispersion, promoting disintegration and the like. However, recent research found that a pharmaceutical preparation containing sodium lauryl sulfate suffers drawbacks as regards stability. More specifically, the preparation containing sodium lauryl sulfate is easily colored into brown and is gradually deteriorated with time. Further, when the discolored and deteriorated preparation containing sodium lauryl sulfate is administered to a patient or a subject, the preparation displays-undesirable behavior, e.g., the pharmacological substance is dissolved out from the preparation at a higher rate than designed.

Nevertheless, no method for stabilizing a pharmaceutical preparation containing sodium lauryl sulfate has been proposed heretofore.

DISCLOSURE OF THE INVENTION

An object of the present invention is to provide a method for stabilizing a pharmaceutical preparation containing sodium lauryl sulfate.

Another object of the invention is to provide a sodium lauryl sulfate-containing pharmaceutical preparation excellent in stability during storage and suppressed in discoloration and deterioration.

A further object of the invention is to provide a sodium lauryl sulfate-containing pharmaceutical preparation protected from change in properties, e.g., preventing change in the dissolution rate of the pharmacological substance from the preparation.

The present inventors conducted extensive research to develop a pharmaceutical preparation that, while containing sodium lauryl sulfate, is excellent in storage stability, suppressed in discoloration and deterioration, and does not undergo change in properties, e.g., no change in the dissolution rate of pharmacological substance from the preparation. Consequently, the inventors found that the objects of the invention can be achieved by incorporating into the preparation at least one member selected from the group consisting of neutral salts and basic substances. The present invention was completed based on this novel finding.

According to the invention, there is provided a method for stabilizing a pharmaceutical preparation containing a pharmacological substance and sodium lauryl sulfate, the method comprising incorporating into the preparation at least one member selected from the group consisting of neutral salts and basic substances.

According to the invention, there is provided a pharmaceutical preparation comprising (1) a pharmacological substance, (2) sodium lauryl sulfate, and (3) at least one member selected from the group consisting of neutral salts and basic substances.

According to the invention, there is provided a sodium lauryl sulfate-containing pharmaceutical preparation excellent in storage stability and suppressed in discoloration and deterioration.

According to the invention, there is provided a sodium lauryl sulfate-containing pharmaceutical preparation free from change of properties, e.g., free from a change of the rate at which the pharmacological substance is dissolved out from the preparation.

Pharmacological substances to be used in the invention are not limited. A wide variety of such substances can be used and include those to be contained in preparations for inhibiting platelet aggregation, preparations for central nerve, preparations for peripheral nerve, preparations for circulatory organs, preparations for respiratory organs, preparations for digestive organs, hormone preparations, vitamin preparations, anti-allergic preparations, anti-tumor preparations, antibiotic preparations, chemotherapeutic preparations, and so on. Specific examples of such pharmacological substances are cilostazol, ticlopidine hydrochloride, ethyl icosapentate, beraprost sodium, sarpogrelate hydrochloride, etc.

According to the invention, at least one member selected from the group consisting of neutral salts and basic substances, preferably at least one basic substance, is added to a preparation containing a pharmacological substance and sodium lauryl sulfate.

A wide variety of known neutral salts that are pharmaceutically acceptable can be used as the neutral salt. Useful neutral salts are, for example, sodium chloride, potassium chloride and like alkali metal chlorides.

Useful basic substances include, for example, basic salts, metal oxides, metal hydroxides, etc.

Basic salts to be used include a wide variety of known basic salts that are pharmaceutically acceptable. Examples are aluminum silicate, magnesium silicate, calcium silicate and like silicates; sodium hydrogen carbonate, magnesium carbonate, calcium carbonate and like carbonates; magnesium stearate, aluminum stearate, calcium steatrate and like stearates; sodium citrate, potassium citrate, calcium citrate and like citrates; anhydrous sodium monohydrogen phosphate, trisodium phosphate and like phosphates; synthetic hydrotalcite, magnesium silicate aluminate, magnesium bismuth silicate aluminate, magnesium metasilicate aluminate and the like.

Metal oxides to be used include a wide variety of known metal oxides that are pharmaceutically acceptable. Examples are magnesium oxide, calcium oxide, aluminum oxide, zinc oxide, iron oxide, copper oxide, nickel oxide, manganese oxide, titanium oxide, etc.

Metal hydroxides to be used include a wide variety of known pharmaceutically acceptable metal hydroxides. Examples are aluminum hydroxide, magnesium hydroxide, aluminum hydroxide dried gel and the like.

Basic substances are preferred in the invention. More specifically, it is preferable to use silicates, carbonates, stearates, citrates, phosphates, metal oxides and metal hydroxides. Further, citrates, metal oxides and metal hydroxides are more preferable among which metal oxides and metal hydroxides are most preferable.

Sodium citrate is preferred as citrate. Magnesium oxide is preferred as metal oxide. Magnesium hydroxide is preferred as metal hydroxide.

At least one compound selected from the group consisting of neutral salts and basic substances can be used either alone or in combination of two or more in the invention.

The amount of at least one species selected from the group consisting of neutral salts and basic substances is at least 0.01 wt %, preferably at least 0.05 wt %, more preferably at least 0.3 wt %, especially preferably at least 0.5 wt %, relative to the weight of sodium lauryl sulfate contained in the preparation of the invention. From an economical viewpoint, the amount of the above-mentioned compound is up to 2000 wt %, preferably up to 1500 wt %, more preferably up to 1300 wt %, especially preferably up to 1000 wt %, relative to the weight of sodium lauryl sulfate present in the preparation of the invention.

When at least one compound selected from the group consisting of neutral salts and basic substances is water-soluble, it may be incorporated into the preparation as such or as an aqueous solution in the course of production of the preparation. A water-insoluble compound may be incorporated as such in the preparation process of the preparation. Irrespective of its solubility in water, the particle size of the compound incorporated as such is preferably as small as possible.

The pharmaceutical preparation containing sodium lauryl sulfate according to the invention may take any of conventional dosage forms insofar as it is in a solid form. Typical examples of the dosage forms are tablets, fine granules, granules, powder, pills, capsules, etc. The preparation of the invention can be prepared by known methods.

The preparation containing sodium lauryl sulfate according to the invention can be prepared with conjoint use of properly selected known additives such as excipients, binders, disintegrators, absorption accelerators, humectants, adsorbents, lubricants, controlled release bases, etc.

Excipients to be used include a wide range of known excipients usually employed in preparing pharmaceutical preparations. Examples are lactose, sucrose, sodium chloride, glucose, urea, starch, kaolin, microcrystalline cellulose, silicic acid, cacao butter, hydrogenated vegetable oil, talc, etc.

Binders to be used include a wide range of known binders customarily employed in pharmaceutical preparations. Examples are water, ethanol, propanol, simple syrup, glucose solution, starch solution, gelatin solution, carboxymethyl cellulose, shellac, methyl cellulose, hydroxypropyl cellulose, hydroxypropylmethyl cellulose, polyvinyl pyrrolidone, gum arabic powder, tragacanth powder, etc.

Disintegrators to be used include a wide range of known disintegrators usually used in pharmaceutical preparations. Examples are low substituted hydroxypropyl cellulose, sodium carboxymethyl starch, crosscarmellose sodium, carboxymethylcellulose, microcrystalline cellulose, crospovidone, etc.

Absorption accelerators to be used may be those known accelerators normally employed for pharmaceutical preparations. Examples are quaternary ammonium base, sugar ester, etc.

Humectants to be used are selected from various known humectants employed for pharmaceutical preparations. Examples are glycerin, starch, etc.

Adsorbents to be used include a wide range of known adsorbents employed in preparing pharmaceutical preparations. Examples are starch, lactose, kaolin, bentonite, colloidal silica, etc.

Lubricants to be used include a wide range of known lubricants employed for pharmaceutical preparations. Examples are stearates such as magnesium stearate, aluminum stearate, calcium stearate and the like, refined talc, boric acid powder, polyethylene glycol, hydrogenated oil, etc.

Controlled release bases to be used include a wide range of known bases employed in pharmaceutical preparations. Examples are ethyl cellulose, hydroxypropyl cellulose, hydroxypropylmethyl cellulose, hydroxypropylmethyl cellulose phthalate, hydroxypropylmethyl cellulose acetate succinate, carboxymethylethyl cellulose, methyl cellulose, sodium carboxymethylcellulose, polyvinyl pyrrolidone, polyvinyl alcohol, polyvinyl acetal diethylaminoacetate, aminoacryl methacrylate copolymer-E, aminoacryl methacrylate copolymer-RS, methacrylic acid copolymer-L, methacrylic acid copolymer-LD, methacrylic acid copolymer-S, ethyl acrylate-methyl methacrylate copolymer, etc.

The above-mentioned additional components can be used either alone or in combination.

The tablets may be coated in the conventional manner when so required. For example, the tablet may be sugar-coated, gelatin-coated, enteric coated, film-coated, coated with a moisture-permeable semi-permeable membrane, double-coated, multi-layer coated, dry coated, etc.

Capsules can be prepared by mixing the pharmacological substance with the above-mentioned components to enclose the former in a hard gelatin capsule, soft gelatin capsule or the like.

Furthermore, the preparation of the invention may contain a coloring agent, preservative, aroma, flavour agent, sweetener, and like known pharmaceutical component(s).

BEST MODE OF CARRYING OUT THE INVENTION

The following examples illustrate the present invention in further detail.

The components used in the examples are as follows.
L-HPC: Low-substituted hydroxypropyl cellulose (trade name: LH-31, Shin-Etsu Chemical Co., Ltd.)
HPMC: Hydroxypropylmethyl cellulose (trade name: Metolose 90SH 4000, Shin-Etsu Chemical Co., Ltd.)
HPC-L: Hydroxypropyl cellulose (trade name: HPC-L, Nippon Soda Co., Ltd.)
Crystalline cellulose: Avicel PH301

EXAMPLES 1 AND 2

Cilostazol, sodium lauryl sulfate (passing through a sieve having openings of 250 μm in size), L-HPC, HPMC and HPC-L were mixed together in the amounts (mg) shown below in Table 1. While adding purified water to the mixture, it was granulated by agitating, and then fluid-bed dried.

Magnesium stearate was mixed with the granules, and the mixture was made into tablets with a punch 7 mm in diameter to give white tablets.

Comparative Example 1

White tablets were prepared in the same manner as in Example 1 with the exception of not further adding magnesium stearate.

TABLE 1

|  | Example 1 | Example 2 | Example 3 |
|---|---|---|---|
| Cilostazol | 80 | 80 | 80 |
| Sodium lauryl sulfate | 15 | 15 | 15 |
| L-HPC | 20 | 20 | 20 |
| HPMC | 10 | 10 | 10 |
| HPC-L | 3 | 3 | 3 |
| Magnesium stearate | 0.1 | 0.4 | 0 |
| Total (mg/tablet) | 128.1 | 128.4 | 128.0 |

Test Example 1

The tablets prepared in Examples 1 and 2 and Comparative Example 1 were stored for a week under 60° C. temperature conditions to observe the discoloration of tablets. The tablets of Comparative Example 1 exhibited brown discoloration, while the tablets of Examples 1 and 2 containing magnesium stearate exhibited only slight brown discoloration, clearly indicating that discoloration had been suppressed.

Test Example 2

As to the tablets prepared in Example 2, the dissolution rate of the pharmacological substance (cilostazol) before or after 1-week storage at 60° C. was examined. This test was carried out by a paddle method (75 rpm) using 720 ml of an aqueous solution of 0.3% sodium lauryl sulfate as a test solution.

The results showed that no difference was found between the dissolution rates of the pharmacological substance before and after 1-week storage at 60° C. of the tablets prepared in Example 2.

EXAMPLES 3 AND 4

Cilostazol, sodium lauryl sulfate (passing through a sieve having openings of 250 μm in size), L-HPC, HPMC and HPC-L were mixed together in the amounts (mg) shown below in Table 2. While adding purified water to the mixture, it was granulated by agitating, and then fluid-bed dried.

As a separate procedure, magnesium stearate was mixed with sodium lauryl sulfate (passing through a sieve having openings of 500 μm in size) to give granules.

The two kinds of granules were mixed in the amounts shown in Table 2 and the mixture was made into tablets with a punch of 7 mm in diameter to give white tablets.

EXAMPLES 5 AND 6

Cilostazol, sodium lauryl sulfate (passing through a sieve having openings of 250 μm in size), L-HPC, HPMC and HPC-L were mixed together in the amounts (mg) shown below in Table 2. While adding an aqueous solution of sodium citrate to the mixture, it was granulated by agitating, and fluid-bed dried.

As a separate procedure, magnesium stearate was mixed with sodium lauryl sulfate (passing through a sieve having openings of 500 μm in size) to give granules.

The two kinds of granules were mixed in the amounts shown in Table 2 and the mixture was made into tablets with a punch of 7 mm in diameter to give white tablets.

TABLE 2

|  | Example 3 | Example 4 | Example 5 | Example 6 |
| --- | --- | --- | --- | --- |
| Cilostazol | 80 | 80 | 80 | 80 |
| Sodium lauryl sulfate | 4 | 8 | 4 | 4 |
| L-HPC | 20 | 20 | 20 | 20 |
| HPMC | 10 | 10 | 10 | 10 |
| HPC-L | 4.6 | 4.6 | 4.6 | 4.6 |
| Sodium citrate | 0 | 0 | 3 | 3 |
| Sodium lauryl sulfate | 11 | 7 | 11 | 11 |
| Magnesium stearate | 0.4 | 0.4 | 0.4 | 0.6 |
| Total (mg/tablet) | 130 | 130 | 133 | 133.2 |

Test Example 3

The tablets prepared in Examples 3 to 6 were stored under 60° C. temperature conditions for a week to observe the change in the color of the tablets. The results are shown in Table 3.

TABLE 3

|  | Example 3 | Example 4 | Example 5 | Example 6 |
| --- | --- | --- | --- | --- |
| 60° C., one week | Specked white | Specked white | White | White |

The tablets of Examples 5 and 6 containing sodium citrate and magnesium stearate, respectively were more suppressed in coloration and more stabilized than these prepared in Examples 3 and 4 containing only magnesium stearate.

EXAMPLES 7 TO 10

Cilostazol, sodium lauryl sulfate (passing through a sieve having openings of 250 μm in size), L-HPC, HPMC and HPC-L were mixed together in the amounts (mg) shown below in Table 4. While adding an aqueous solution of sodium citrate and/or an aqueous solution of sodium chloride to the mixture, it was granulated by agitating, and then fluid-bed dried.

As a separate procedure, magnesium stearate was mixed with sodium lauryl sulfate (passing through a sieve having openings of 500 μm in size) to give granules.

The two kinds of granules were mixed in the amounts shown in Table 4 and the mixture was made into tablets with a punch of 7 mm in diameter to give white tablets.

TABLE 4

|  | Example 7 | Example 8 | Example 9 | Example 10 |
| --- | --- | --- | --- | --- |
| Cilostazol | 80 | 80 | 80 | 80 |
| Sodium lauryl sulfate | 15 | 4 | 12 | 15 |
| L-HPC | 20 | 20 | 20 | 17 |
| HPMC | 10 | 10 | 10 | 10 |
| HPC-L | 4.4 | 4.4 | 4.4 | 4.4 |
| Sodium citrate | 3 | 0 | 3 | 3 |
| Sodium chloride | 0 | 3.3 | 0 | 3 |
| Sodium lauryl sulfate | 0 | 11 | 3 | 0 |
| Magnesium stearate | 0.6 | 0.6 | 0.6 | 0.6 |
| Total (mg/tablet) | 133.0 | 133.3 | 133.0 | 133.0 |

Test Example 4

The tablets prepared in Examples 7 to 10 were stored under 60° C. temperature conditions for 4 weeks or 70° C. temperature conditions for 1 week to observe the change in the color of the tablets. The results are shown in Table 5.

TABLE 5

|  | Example 7 | Example 8 | Example 9 | Example 10 |
| --- | --- | --- | --- | --- |
| 60° C., 4 weeks | Slight specked white | Specked white | Specked white | White (no change) |
| 70° C., one week | Slight specked white | Slight specked white | Slight specked white | White (no change) |

EXAMPLES 11 TO 15

Cilostazol, sodium lauryl sulfate (passing through a sieve having openings of 250 μm in size), L-HPC, HPMC, microcrystalline cellulose and HPC-L were mixed together with magnesium oxide in Examples 12 to 15 in the amounts (mg) shown below in Table 6. While adding an aqueous solution of sodium citrate (Example 11) or purified water (Examples 12 to 15) to the mixture, it was granulated by agitating, and then fluid-bed dried.

Magnesium stearate was mixed with the granules, and the mixture was made into tablets with a punch of 7 mm in diameter to give white tablets.

TABLE 6

|  | Example 11 | Example 12 | Example 13 | Example 14 | Example 15 |
| --- | --- | --- | --- | --- | --- |
| Cilostazol | 80 | 80 | 80 | 80 | 80 |
| Sodium lauryl sulfate | 15 | 15 | 15 | 15 | 15 |
| L-HPC | 20 | 20 | 20 | 19 | 20 |
| HPMC | 0 | 10 | 9 | 9 | 0 |
| Microcrystalline cellulose | 10 | 0 | 0 | 0 | 10 |
| HPC-L | 6.0 | 4.4 | 4.4 | 4.4 | 5.4 |
| Sodium citrate | 5 | 0 | 0 | 0 | 0 |
| Magnesim oxide | 0 | 3 | 6 | 9 | 6 |
| Magnesium stearate | 0.6 | 0.6 | 0.6 | 0.6 | 0.6 |
| Total (mg/tablet) | 136.6 | 133.3 | 135.0 | 137.0 | 137.0 |

Test Example 5

The tablets prepared in Examples 11 to 15 were stored under 60° C. temperature conditions for 2 weeks and 70° C. temperature conditions for 1 week or 2 weeks to observe the change in the color of the tablets. The results are shown in Table 7.

TABLE 7

|  | Example 11 | Example 12 | Example 13 | Example 14 | Example 15 |
| --- | --- | --- | --- | --- | --- |
| 60° C., 2 weeks | White | White | White | White | White |
| 70° C., 1 week | White | White | White | White | White |
| 70° C., 2 weeks | Light brown | Light speckles | White | White | White |

Test Example 6

As to the tablets prepared in Examples 11 and 12, the dissolution rates of the pharmacological substance (cilostazol) before and after 1-week storage at 70° C. were examined. This test was carried out by a paddle method (75 rpm) using 720 ml of an aqueous solution of 0.3% sodium lauryl sulfate as a test solution.

The results showed that no difference was found between the dissolution rates of the pharmacological substance before and after 1-week storage at 70° C. of the tablets prepared in Examples 11 and 12.

The invention claimed is:

1. A method for suppressing discoloration and deterioration of a pharmaceutical preparation caused by sodium lauryl sulfate being contained therein, the method comprising incorporating at least one basic substance selected from the group consisting of metal silicates, metal oxides, and metal hydroxides into a preparation that contains a pharmacological substance, sodium lauryl sulfate, and at least one cellulose selected from a group consisting of low-substituted hydroxypropyl cellulose, hydroxypropylmethyl cellulose, hydroxypropyl cellulose and crystalline cellulose,
   wherein the incorporation of at least one basic substance selected from the group consisting of metal silicates, metal oxides, and metal hydroxides suppresses discoloration and deterioration of a pharmaceutical preparation caused by sodium lauryl sulfate, and
   the pharmaceutical preparation contains 3 to 9 parts by weight of the basic substance per 80 parts by weight of the pharmacological substance.

2. The method according to claim 1, wherein said at least one basic substance selected from the group consisting of metal silicates, metal oxides, and metal hydroxides is incorporated in an amount of 0.5 wt % to 99 wt % relative to the weight of sodium lauryl sulfate.

3. The method according to claim 1, wherein the pharmacological substance is cilostazol.

* * * * *

UNITED STATES PATENT AND TRADEMARK OFFICE
CERTIFICATE OF CORRECTION

PATENT NO.       : 7,867,514 B2
APPLICATION NO.  : 10/276294
DATED            : January 11, 2011
INVENTOR(S)      : Yuso Tomohira et al.

Page 1 of 1

It is certified that error appears in the above-identified patent and that said Letters Patent is hereby corrected as shown below:

On the Title Page, after Item (65), the "Prior Publication Data", and before Item (51), the "Int. Cl." data, insert the following missing data:
-- (30)        Foreign Application Priority Data
May 24, 2000     (JP) ………………… 2000-152969 --.

Signed and Sealed this
Sixth Day of August, 2013

Teresa Stanek Rea
*Acting Director of the United States Patent and Trademark Office*